(12) United States Patent
Simmons et al.

(10) Patent No.: US 9,107,990 B2
(45) Date of Patent: Aug. 18, 2015

(54) REDUCED-PRESSURE DRESSINGS, SYSTEMS, AND METHODS FOR USE WITH LINEAR WOUNDS

(75) Inventors: Tyler Simmons, San Antonio, TX (US); Colin John Hall, Poole (GB); Timothy Mark Robinson, Basingstoke (GB)

(73) Assignee: KCI Licensing, Inc., San Antonio, TX (US)

( * ) Notice: Subject to any disclaimer, the term of this patent is extended or adjusted under 35 U.S.C. 154(b) by 798 days.

(21) Appl. No.: 13/305,171

(22) Filed: Nov. 28, 2011

(65) Prior Publication Data
US 2012/0209226 A1 Aug. 16, 2012

Related U.S. Application Data

(60) Provisional application No. 61/442,723, filed on Feb. 14, 2011.

(51) Int. Cl.
*A61M 1/00* (2006.01)
*A61M 27/00* (2006.01)

(52) U.S. Cl.
CPC .................................. *A61M 1/0088* (2013.01)

(58) Field of Classification Search
CPC ............ A61M 1/0066; A61M 1/0013; A61M 1/0023; A61M 1/0088; A61M 1/101; A61M 1/1037; A61M 1/1046; A61M 1/1053; A61M 1/14; A61M 5/14228; A61M 5/14232; A61M 27/00; A61M 2001/0017; A61M 2205/12; A61M 2013/00536; A61M 1/00; F04B 43/00; F04B 43/06; F04B 43/073; F04B 43/0733; F04B 43/12; F04B 45/00; F04B 45/06; F04B 49/02; F04B 53/16; F04B 2205/00; F04B 2207/04; F04B 2207/70

USPC ................. 604/6.11, 313, 319; 210/645, 646; 417/85, 238, 244, 268
See application file for complete search history.

(56) References Cited

U.S. PATENT DOCUMENTS

| 1,355,846 | A | 10/1920 | Rannells |
| 2,547,758 | A | 4/1951 | Keeling |
| 2,632,443 | A | 3/1953 | Lesher |

(Continued)

FOREIGN PATENT DOCUMENTS

| AU | 550575 A1 | 8/1982 |
| AU | 745271 | 4/1999 |

(Continued)

OTHER PUBLICATIONS

N.A. Bagautdinov, "Variant of External Vacuum Aspiration in the Treatment of Purulent Diseases of the Soft Tissues," *Current Problems in Modern Clinical Surgery: Interdepartmental Collection*, edited by V. Ye Volkov et al. (Chuvashia State University, Cheboksary, U.S.S.R. 1986);pp. 94-96.

(Continued)

*Primary Examiner* — Melanie Hand (57) ABSTRACT

Systems, methods, and dressings for treating a linear wound, such as an incision, on a patient are presented. The systems, dressings, and methods include a sealing ring that helps form a fluid seal around the linear wound. In one instance, a sealing material is extruded around the linear wound to help form a seal. In another instance, a sealing ring is coupled to a lower portion of a dressing bolster to form a seal. Other systems, methods, and apparatuses are disclosed.

26 Claims, 10 Drawing Sheets

(56) References Cited

U.S. PATENT DOCUMENTS

| | | | |
|---|---|---|---|
| 2,682,873 | A | 7/1954 | Evans et al. |
| 2,910,763 | A | 11/1959 | Lauterbach |
| 2,969,057 | A | 1/1961 | Simmons |
| 3,066,672 | A | 12/1962 | Crosby, Jr. et al. |
| 3,367,332 | A | 2/1968 | Groves |
| 3,520,300 | A | 7/1970 | Flower, Jr. |
| 3,568,675 | A | 3/1971 | Harvey |
| 3,648,692 | A | 3/1972 | Wheeler |
| 3,682,180 | A | 8/1972 | McFarlane |
| 3,826,254 | A | 7/1974 | Mellor |
| 4,080,970 | A | 3/1978 | Miller |
| 4,096,853 | A | 6/1978 | Weigand |
| 4,139,004 | A | 2/1979 | Gonzalez, Jr. |
| 4,165,748 | A | 8/1979 | Johnson |
| 4,184,510 | A | 1/1980 | Murry et al. |
| 4,233,969 | A | 11/1980 | Lock et al. |
| 4,245,630 | A | 1/1981 | Lloyd et al. |
| 4,256,109 | A | 3/1981 | Nichols |
| 4,261,363 | A | 4/1981 | Russo |
| 4,275,721 | A | 6/1981 | Olson |
| 4,284,079 | A | 8/1981 | Adair |
| 4,297,995 | A | 11/1981 | Golub |
| 4,333,468 | A | 6/1982 | Geist |
| 4,373,519 | A | 2/1983 | Errede et al. |
| 4,382,441 | A | 5/1983 | Svedman |
| 4,392,853 | A | 7/1983 | Muto |
| 4,392,858 | A | 7/1983 | George et al. |
| 4,419,097 | A | 12/1983 | Rowland |
| 4,465,485 | A | 8/1984 | Kashmer et al. |
| 4,475,909 | A | 10/1984 | Eisenberg |
| 4,480,638 | A | 11/1984 | Schmid |
| 4,525,166 | A | 6/1985 | Leclerc |
| 4,525,374 | A | 6/1985 | Vaillancourt |
| 4,540,412 | A | 9/1985 | Van Overloop |
| 4,543,100 | A | 9/1985 | Brodsky |
| 4,548,202 | A | 10/1985 | Duncan |
| 4,551,139 | A | 11/1985 | Plaas et al. |
| 4,569,348 | A | 2/1986 | Hasslinger |
| 4,605,399 | A | 8/1986 | Weston et al. |
| 4,608,041 | A | 8/1986 | Nielsen |
| 4,640,688 | A | 2/1987 | Hauser |
| 4,655,754 | A | 4/1987 | Richmond et al. |
| 4,664,662 | A | 5/1987 | Webster |
| 4,710,165 | A | 12/1987 | McNeil et al. |
| 4,733,659 | A | 3/1988 | Edenbaum et al. |
| 4,743,232 | A | 5/1988 | Kruger |
| 4,758,220 | A | 7/1988 | Sundblom et al. |
| 4,787,888 | A | 11/1988 | Fox |
| 4,826,494 | A | 5/1989 | Richmond et al. |
| 4,838,883 | A | 6/1989 | Matsuura |
| 4,840,187 | A | 6/1989 | Brazier |
| 4,863,449 | A | 9/1989 | Therriault et al. |
| 4,872,450 | A | 10/1989 | Austad |
| 4,878,901 | A | 11/1989 | Sachse |
| 4,897,081 | A | 1/1990 | Poirier et al. |
| 4,906,233 | A | 3/1990 | Moriuchi et al. |
| 4,906,240 | A | 3/1990 | Reed et al. |
| 4,919,654 | A | 4/1990 | Kalt |
| 4,941,882 | A | 7/1990 | Ward et al. |
| 4,953,565 | A | 9/1990 | Tachibana et al. |
| 4,969,880 | A | 11/1990 | Zamierowski |
| 4,985,019 | A | 1/1991 | Michelson |
| 5,037,397 | A | 8/1991 | Kalt et al. |
| 5,086,170 | A | 2/1992 | Luheshi et al. |
| 5,092,858 | A | 3/1992 | Benson et al. |
| 5,100,396 | A | 3/1992 | Zamierowski |
| 5,134,994 | A | 8/1992 | Say |
| 5,149,331 | A | 9/1992 | Ferdman et al. |
| 5,167,613 | A | 12/1992 | Karami et al. |
| 5,176,663 | A | 1/1993 | Svedman et al. |
| 5,215,522 | A | 6/1993 | Page et al. |
| 5,232,453 | A | 8/1993 | Plass et al. |
| 5,261,893 | A | 11/1993 | Zamierowski |
| 5,278,100 | A | 1/1994 | Doan et al. |
| 5,279,550 | A | 1/1994 | Habib et al. |
| 5,298,015 | A | 3/1994 | Komatsuzaki et al. |
| 5,342,376 | A | 8/1994 | Ruff |
| 5,344,415 | A | 9/1994 | DeBusk et al. |
| 5,358,494 | A | 10/1994 | Svedman |
| 5,437,622 | A | 8/1995 | Carion |
| 5,437,651 | A | 8/1995 | Todd et al. |
| 5,527,293 | A | 6/1996 | Zamierowski |
| 5,549,584 | A | 8/1996 | Gross |
| 5,556,375 | A | 9/1996 | Ewall |
| 5,607,388 | A | 3/1997 | Ewall |
| 5,636,643 | A | 6/1997 | Argenta et al. |
| 5,645,081 | A | 7/1997 | Argenta et al. |
| 6,071,267 | A | 6/2000 | Zamierowski |
| 6,135,116 | A | 10/2000 | Vogel et al. |
| 6,241,747 | B1 | 6/2001 | Ruff |
| 6,287,316 | B1 | 9/2001 | Agarwal et al. |
| 6,345,623 | B1 | 2/2002 | Heaton et al. |
| 6,488,643 | B1 | 12/2002 | Tumey et al. |
| 6,493,568 | B1 | 12/2002 | Bell et al. |
| 6,553,998 | B2 | 4/2003 | Heaton et al. |
| 6,814,079 | B2 | 11/2004 | Heaton et al. |
| 2002/0077661 | A1 | 6/2002 | Saadat |
| 2002/0115951 | A1 | 8/2002 | Norstrem et al. |
| 2002/0120185 | A1 | 8/2002 | Johnson |
| 2002/0143286 | A1 | 10/2002 | Tumey |
| 2003/0144619 | A1* | 7/2003 | Augustine .................... 602/2 |
| 2005/0101940 | A1 | 5/2005 | Radl et al. |
| 2009/0076431 | A1* | 3/2009 | Budig et al. ................. 602/46 |
| 2009/0092659 | A1* | 4/2009 | Dale et al. ................... 424/447 |
| 2009/0227969 | A1 | 9/2009 | Jaeb et al. |
| 2009/0312728 | A1* | 12/2009 | Randolph et al. ........... 604/319 |
| 2010/0185163 | A1 | 7/2010 | Heagle |
| 2012/0219544 | A1* | 8/2012 | Asada et al. ............... 424/130.1 |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0355802 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| JP | 4129536 | 4/1992 |
| SG | 71559 | 4/2002 |
| WO | WO 80/02182 | 10/1980 |
| WO | WO 87/04626 | 8/1987 |
| WO | WO 90/10424 | 9/1990 |
| WO | WO 93/09727 | 5/1993 |
| WO | WO 94/20041 | 9/1994 |
| WO | WO 96/05873 | 2/1996 |
| WO | WO 97/18007 | 5/1997 |
| WO | WO 99/13793 | 3/1999 |
| WO | WO 2008/008032 | 1/2008 |

OTHER PUBLICATIONS

Louis C. Argenta, MD and Michael J. Morykwas, PhD; "Vacuum-Assisted Closure: A New Method for Wound Control and Treatment: Clinical Experience"; Annals of Plastic Surae , vol. 38, No. 6, Jun. 1997; pp. 563-576.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

(56) References Cited

OTHER PUBLICATIONS

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, Oct 1988, pp. 48-52, and 8 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

K.F. Jeter, T.E. Tintle, and M. Chariker, "Managing Draining Wounds and Fistulae: "New and Established Methods, *Chronic Wound Care*, edited by D. Krasner (Health Management Publications, Inc., King of Prussia, PA 1990), pp. 240-246.

G. Živadinović, V. Đukić, Ž. Maksimović, Đ. Radak, and P. Peška, "Vacuum Therapy in the Treatment of Peripheral Blood Vessels," *Timok Medical Journal* 11 (1986), pp. 161-164.

F.E. Johnson, "An Improved Technique for Skin Graft Placement Using a Suction Drain," *Surgery, Gynecology, and Obstetrics* 159 (1984), pp. 584-585.

A.A. Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967).

M. Schein, R. Saadia, J.R. Jamieson, and G.A.G. Decker, "The 'Sandwich Technique' in the Management of the Open Abdomen," *British Journal of Surgery* 73 (1986), pp. 369-370.

D.E. Tribble, An Improved Sump Drain-Irrigation Device of Simple Construction, *Archives of Surgery* 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," *Annals of Plastic Surgery* 38 (1997), pp. 553-562 (Morykwas I).

C.E. Tennants, "The Use of Hypermia in the Postoperative Treatment of Lesions of the Extremities and Thorax," *Journal of the American Medical Association* 64 (1915), pp. 1548-1549.

Selections from W. Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. ® Therapy Clinical Guidelines: A Reference Source for Clinicians (Jul. 2007).

International Search Report for PCT International Application PCT/US2011/062422 filed Nov. 29, 2011 mailed Feb. 27, 2012.

\* cited by examiner

REDUCED-PRESSURE DRESSINGS, SYSTEMS, AND METHODS FOR USE WITH LINEAR WOUNDS

RELATED APPLICATION

The present invention claims the benefit, under 35 USC §119(e), of the filing of U.S. Provisional Patent Application Ser. No. 61/442,723, entitled "Reduced-Pressure Dressings, Systems, and Methods for Use with Linear Wounds," filed 14 Feb. 2011, which is incorporated herein by reference for all purposes.

BACKGROUND

The present disclosure relates generally to medical treatment systems and, more particularly, but not by way of limitation, to reduced pressure dressings, systems, and methods for treating linear wounds.

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, which may include faster healing and increased formulation of granulation tissue. Typically, reduced pressure is applied to tissue through a porous pad or other manifold device. The porous pad distributes reduced pressure to the tissue and channels fluids that are drawn from the tissue.

SUMMARY

According to an illustrative embodiment, a system for treating a linear wound on a patient includes a dressing assembly. As used herein, "linear wound" refers generally to a laceration or incision whether in a line or not. The dressing assembly includes a dressing bolster having a first side and a second, inward-facing side; a comfort layer coupled to the second, inward-facing side of the dressing bolster; a first sealing member portion covering the dressing bolster; and a second sealing member portion covering a portion of the second, inward-facing side of the dressing bolster and extending outward from the dressing bolster to form a drape extension. A portion of the first sealing member is coupled to the second sealing member. The dressing assembly also includes sealing ring disposed adjacent to the second, inward-facing side of the dressing bolster. The first sealing member portion, second sealing member portion, and sealing ring form a sealed space over the linear wound. The system further comprises a reduced-pressure source for fluidly coupling to the sealed space.

According to another illustrative embodiment, a method for treating a linear wound on a patient with reduced pressure comprises extruding a sealing material around the linear wound to form a sealing ring, disposing a dressing bolster proximate to the linear wound and adjacent to at least a portion of the sealing material, covering the dressing bolster and a portion of the patient's epidermis with a sealing member to create a sealed space, and delivering reduced pressure to the sealed space.

According to another illustrative embodiment, a method for treating a linear wound of a patient with reduced pressure includes disposing a bolster assembly proximate to the linear wound. The bolster assembly includes a dressing bolster having a first side and a second, inward-facing side; a comfort layer coupled to the second, inward-facing side of the dressing bolster; and a sealing ring coupled to the second, inward-facing side of the comfort layer. The method further includes covering the bolster assembly with a sealing member to form a sealed space containing the dressing assembly and introducing reduced pressure into the sealed space.

According to another illustrative embodiment, a system for treating a linear wound on a patient includes a dressing bolster assembly. The dressing bolster assembly includes a dressing bolster having a first side and a second, inward-facing side and a comfort layer coupled to the second, inward-facing side of the dressing bolster. The dressing bolster assembly also includes a comfort layer having a first side and a second, inward-facing side and a sealing ring coupled to the second, inward-facing side of the comfort layer. The system further includes a sealing member disposed over the dressing bolster for creating a sealed space and includes a reduced-pressure source fluidly coupled to the sealed space.

Other features and advantages of the illustrative embodiments will become apparent with reference to the drawings and detailed description that follow.

DETAILED DESCRIPTION OF ILLUSTRATIVE EMBODIMENTS

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

Figure 1:
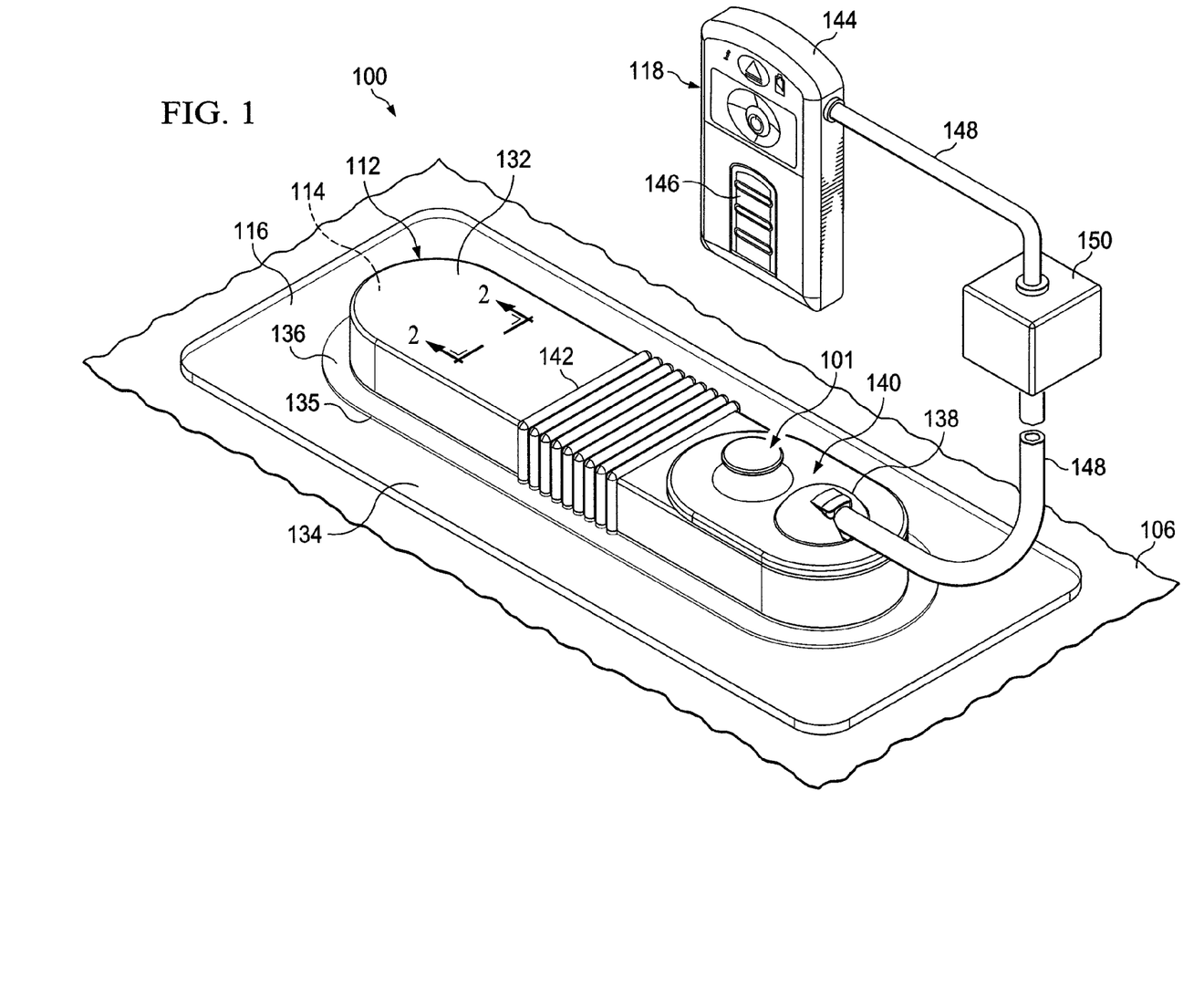
FIG. 1 is a schematic, perspective view of an illustrative system for treating a linear wound with reduced pressure.
Figure 2:
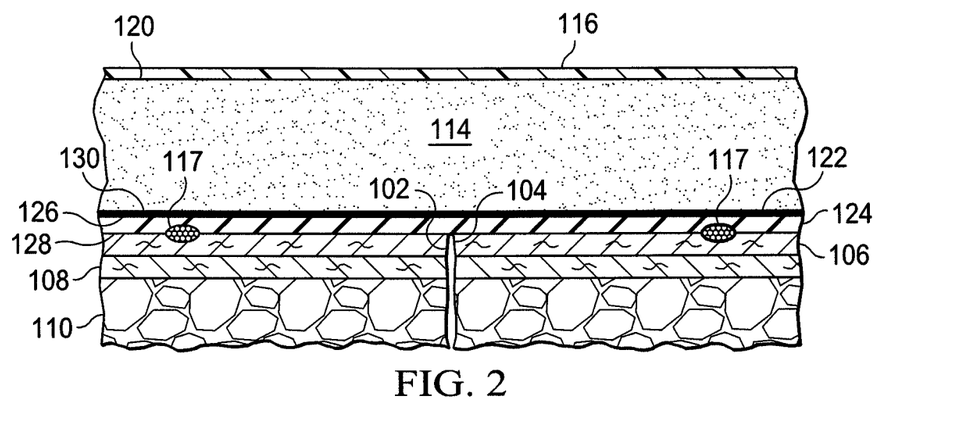
FIG. 2 is a schematic cross section of a portion of the dressing assembly of FIG. 1 taken along line 2-2.

Referring primarily to FIGS. 1 and 2, an illustrative, non-limiting embodiment of a reduced-pressure treatment system 100 for treating a tissue site 102, such as a an incision 104, is presented. The incision 104 is shown extending through or involving epidermis 106, dermis 108, and subcutaneous tissue 110. The reduced-pressure treatment system 100 may also be used with other tissue sites.

The reduced-pressure treatment system 100 includes a dressing assembly 112 having a dressing bolster 114, or manifold member 114. In addition, the reduced-pressure treatment system 100 includes a sealing member 116 and a reduced-pressure subsystem 118. The reduced-pressure treatment system 100 may also include a reduced-pressure indicator 101. While the reduced-pressure treatment system 100 is shown in the context of a reduced-pressure dressing over an incision 104, it should be understood that the reduced-pressure treatment system 100 may be used on other tissue sites, including open wounds.

The dressing bolster 114 has a first side 120 and a second, inward-facing side 122. The dressing bolster 114 may be formed from any bolster material or manifold material that provides a vacuum space, or treatment space, such as a porous and permeable foam or foam-like material, a member formed with pathways, a graft, or gauze. Unless otherwise indicated, as used throughout this document, "or" does not require mutual exclusivity. As a more specific, non limiting example, the dressing bolster 114 may be a reticulated, open-cell polyurethane or polyether foam that allows good permeability of wound fluids while under a reduced pressure. One such foam material that has been used is a VAC® GranuFoam® material available from Kinetic Concepts, Inc. (KCI) of San Antonio, Tex. Any material or combination of materials may be used for the manifold material provided that the manifold material is operable to distribute the reduced pressure. The term "manifold" as used herein generally refers to a substance or structure that is provided to assist in applying reduced pressure to, delivering fluids to, or removing fluids from a tissue site. A manifold typically includes a plurality of flow channels or pathways. The plurality of flow channels may be interconnected to improve distribution of fluids provided to and removed from the area of tissue around the manifold. Examples of manifolds may include, without limitation, devices that have structural elements arranged to form flow channels, cellular foam, such as open-cell foam, porous tissue collections, and liquids, gels, and foams that include or cure to include flow channels.

The reticulated pores of the GranuFoam® material are helpful in carrying out the manifold function, but again other materials may be used. A material with a higher, or lower, density (smaller pore size) than GranuFoam® material may be desirable in some situations. Among the many possible materials, the following may be used: GranuFoam® material, FXI technical foam (www.fxi.com), gauze, a flexible channel-containing member, a graft, etc. In some instances it may be desirable to add ionic silver to the foam in a micro bonding process or to add other substances to the material, such as antimicrobial agents.

A comfort layer 124, which has a first side 126 and a second, inward-facing side 128, may be coupled, e.g., by a heat bond 130 or any other technique, to the second side 122 of the dressing bolster 114. The comfort layer 124 is typically to help provide for patient comfort when the dressing bolster 114 is placed adjacent to the patient's epidermis 106. The comfort layer 124 may be any material that helps prevent skin irritation and discomfort while allowing fluid transmission through the comfort layer 124. As non-limiting examples, a woven, elastic material, a polyester knit textile substrate, a non-woven, or a fenestrated film may be used. As another non-limiting example, an InterDry™ textile material from Milliken Chemical, a division of Milliken & Company, Inc. of Spartanburg, S.C., may be used. The comfort layer 124 may include anti-microbial substances, such as silver.

The dressing bolster 114 may include a plurality of flexibility notches or recesses (not explicitly shown but analogous to notches 218 in FIG. 4) that may be lateral cuts in the dressing bolster 114 on the first side 120. The dressing bolster 114 may include one or more longitudinal cuts or notches. The flexibility notches enhance flexibility of the dressing bolster 114. The enhanced flexibility may be particularly useful when the dressing assembly 112 is applied over a patient's joint or other area of movement. The flexibility notches may also take various shapes, such as hexagons, slits, or squares.

The dressing bolster 114 may be formed with lateral edges that are orthogonal with respect to the second, inward-facing side 122 of the dressing bolster 114. The lateral edges may also be formed with a beveled edge or angled edge. The angled or beveled edge may help distribute shear stress between the dressing bolster and the patient's epidermis 106.

The sealing member 116 provides a fluid seal over the dressing bolster 114 and at least a portion of the patient's epidermis 106. As such, the sealing member 116 may be formed from any material that allows for a fluid seal. "Fluid seal," or "seal," means a seal adequate to maintain reduced pressure at a desired site given the particular reduced-pressure source or subsystem involved. The sealing member 116 may be sealed against epidermis 106 or against a gasket or drape by a sealing apparatus, such as a pressure-sensitive adhesive.

The sealing apparatus may take numerous forms, such as an adhesive sealing tape, or drape tape or strip; double-side drape tape; pressure-sensitive adhesive; paste; hydrocolloid; hydrogel; or other sealing means. If a tape is used, the tape may be formed of the same material as the sealing member 116 with a pre-applied, pressure-sensitive adhesive. The pressure-sensitive adhesive may be applied on a second, inward-facing side of the sealing member 116 or portion thereof. The pressure-sensitive adhesive helps provide a fluid seal between the sealing member 116 and the epidermis 106 which, as used herein, is also deemed to include a gasket or drape against the epidermis 106. Before the sealing member 116 is secured to the epidermis, removable strips, or release liners, covering the pressure-sensitive adhesive may be removed.

The sealing member 116 may be an elastomeric material or any material or substance that provides a fluid seal. "Elastomeric" means having the properties of an elastomer and generally refers to a polymeric material that has rubber-like properties. More specifically, most elastomers have ultimate elongations greater than 100% and a significant amount of resilience. The resilience of a material refers to the material's ability to recover from an elastic deformation. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane, EVA film, co-polyester, and silicones. Further still, sealing member materials may include a silicone drape, 3M Tegaderm® drape, acrylic drape such as one available from Avery Dennison, or an incise drape.

The sealing member 116 may include a first sealing member portion 132 and a second sealing member portion 134. The first sealing member portion 132 extends over the first side 120 of the dressing bolster 114. The sealing member 116 extends further to form a sealing member flange, or sealing member extension 136, which has a first side and a second, inward-facing side (not explicitly shown). An aperture (not explicitly shown but analogous to 234 in FIG. 3) is formed on a portion of the sealing member 116 to allow fluid communication with a reduced-pressure interface 138, which may be part of a reduced-pressure assembly 140.

The second, inward-facing side of the sealing member extension 136 is placed on a first side (top side for the orientation of FIG. 1) of the second sealing member portion 134 and coupled, such as by an adhesive, bond 135, welding (e.g., ultrasonic or RF welding), or cements. Alternatively, the first sealing member portion 132 and second sealing member portion 134 may be integrally formed. The first sealing member portion 132 may include a plurality of bellows 142, folds, or stretch zones. The bellows 142 allow additional drape material to become available, to stretch, or to move, if needed. For example, if the dressing assembly 112 is used on a joint, when the joint is flexed, additional drape material may be necessary or movement necessary. The bellows 142 facilitate such movement.

Prior to application, one or more release members (not shown but analogous to 242 in FIG. 5) may be releasably coupled to the first side of the second sealing member portion 134. The release members provide stiffness and help during deployment of the dressing assembly 112. The release members are typically either casting paper or a film held on the first side of the second sealing member portion 134.

The reduced-pressure subsystem 118 includes a reduced-pressure source 144, which can take many different forms. The reduced-pressure source 144 provides reduced pressure as a part of the reduced-pressure treatment system 100. The reduced-pressure source 144 is fluidly coupled to the reduced-pressure interface 138 by a reduced-pressure delivery conduit 148.

As used herein, "reduced pressure" generally refers to a pressure less than the ambient pressure at a tissue site 102 that is being subjected to treatment. In most cases, this reduced pressure will be less than the atmospheric pressure at which the patient is located. Alternatively, the reduced pressure may be less than a hydrostatic pressure at a tissue site. Unless otherwise indicated, quantitative values of pressure stated herein are gauge pressures.

The reduced pressure delivered to the dressing bolster 114 may be constant or varied (patterned or random) and may be delivered continuously or intermittently. Although the terms "vacuum" and "negative pressure" may be used to describe the pressure applied to the tissue site, the actual pressure applied to the tissue site may be more than the pressure normally associated with a complete vacuum. Consistent with the use herein, unless otherwise indicated, an increase in reduced pressure or vacuum pressure typically refers to a relative reduction in absolute pressure.

The reduced-pressure source 144 is shown having a reservoir region 146, or canister region. An interposed membrane filter, such as hydrophobic or oleophobic filter, may be interspersed between the reduced-pressure delivery conduit 148 and the reduced-pressure source 144. One or more devices, such as a representative device 150, may be fluidly coupled to the reduced-pressure delivery conduit 148. The device 150 may be, for example, another fluid reservoir, or collection member to hold exudates and other fluids removed, a pressure-feedback device, a volume detection system, a blood detection system, an infection detection system, a flow monitoring system, or a temperature monitoring system. Multiple devices 150 may be included. One or more of the illustrative devices 150 may be formed integrally to the reduced-pressure source 144.

The reduced-pressure source 144 may be any device for supplying a reduced pressure, such as a vacuum pump, wall suction, or other source. While the amount and nature of reduced pressure applied to a tissue site will typically vary according to the application, the reduced pressure will typically be between −5 mm Hg (−667 Pa) and −500 mm Hg (−66.7 kPa) and more typically between −75 mm Hg (−9.9 kPa) and −300 mm Hg (−39.9 kPa). For example, and not by way of limitation, the pressure may be −12, −12.5, −13, −14, −14.5, −15, −15.5, −16, −16.5, 17, −17.5, −18, −18.5, −19, −19.5, −20, −20.5, −21, −21.5, −22, −22.5, −23, −23.5, −24, −24.5, −25, −25.5, −26, −26.5 kPa or another pressure.

The reduced pressure developed by reduced-pressure source 144 is delivered through the reduced-pressure delivery conduit 148 to the reduced-pressure interface 138. The reduced-pressure interface 138 allows the reduced pressure to be delivered through the sealing member 116 to the dressing bolster 114.

In providing treatment with the reduced-pressure treatment system 100, it may be desirable to know that reduced pressure of at least a certain threshold level is being delivered to the tissue site 102. The reduced-pressure indicator 101 accomplishes this task. The reduced-pressure indicator 101 may be a separate unit fluidly coupled to the sealing member 116 such that reduced pressure from within the sealed space of the sealing member 116 reaches the reduced-pressure indicator 101 or may be associated with the reduced-pressure interface 138 as part of the reduced-pressure assembly 140 as shown. When adequate reduced pressure is present, the reduced-pressure indicator 101 assumes a collapsed position and when inadequate reduced pressure is present the reduced-pressure indicator 101 assumes a non-collapsed position.

Referring primarily to FIG. 2, a sealing ring 117 may be added between the epidermis 106 and the comfort layer 124. The sealing ring 117 may be formed, as an illustrative example, by applying a ring of sealing material. The sealing material may include hydrocolloids, hydrogels, silicone polymers (both crosslinked [gels] and uncrosslinked), natural gums (xanthan, guar, cellulose), other soft polymer gels, for example those based on polyurethanes, and polyolefin gels, and acrylics. The sealing ring 117 may be deployed by hand forming a ring prior to application of the dressing assembly 112, or if initially in a liquid or gel state, may be extruded from an applicator, such as a syringe. Other sealing materials that may be particularly well suited for application by extrusion include water soluble gums such as xanthan, guar, or cellulose, or thick greases, such as silicones.

The sealing ring 117 may help form a fluid seal around the linear wound or incision 104. The epidermis 106 may have recesses, cracks, wrinkles or other discontinuities on the surface that tend to cause leaks. Moreover, folds, buckles, wrinkles or other discontinuities may form in the sealing member 116 that tend to cause leaks. These discontinuities may be a considerable issue for low flow reduced-pressure systems. The sealing ring 117 may help seal any such skin or sealing member discontinuities around the linear wound or incision 104.

Figure 3:
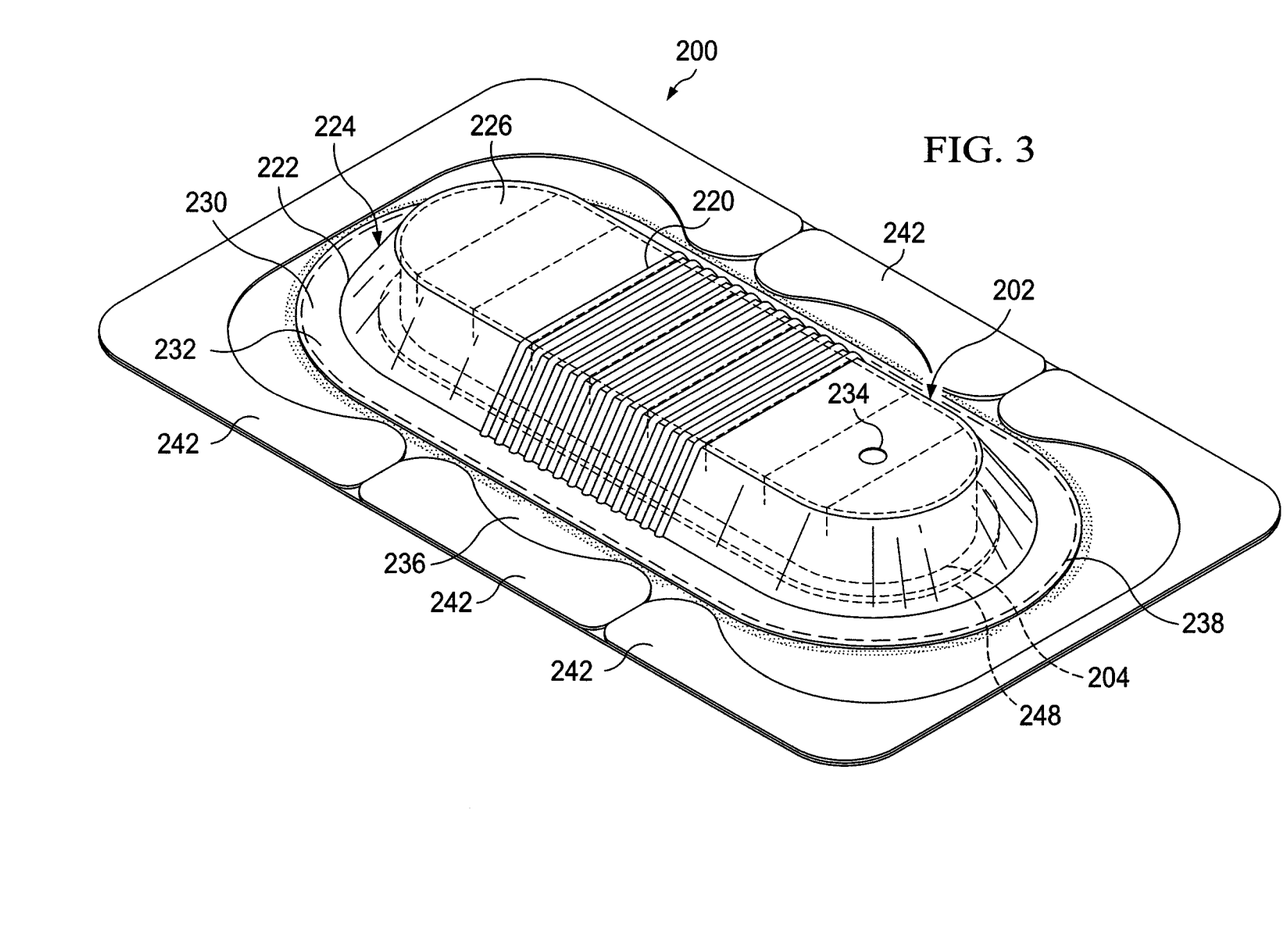
FIG. 3 is a schematic, perspective view of an illustrative embodiment of a portion of a system for treating a linear wound with reduced pressure.
Figure 4:
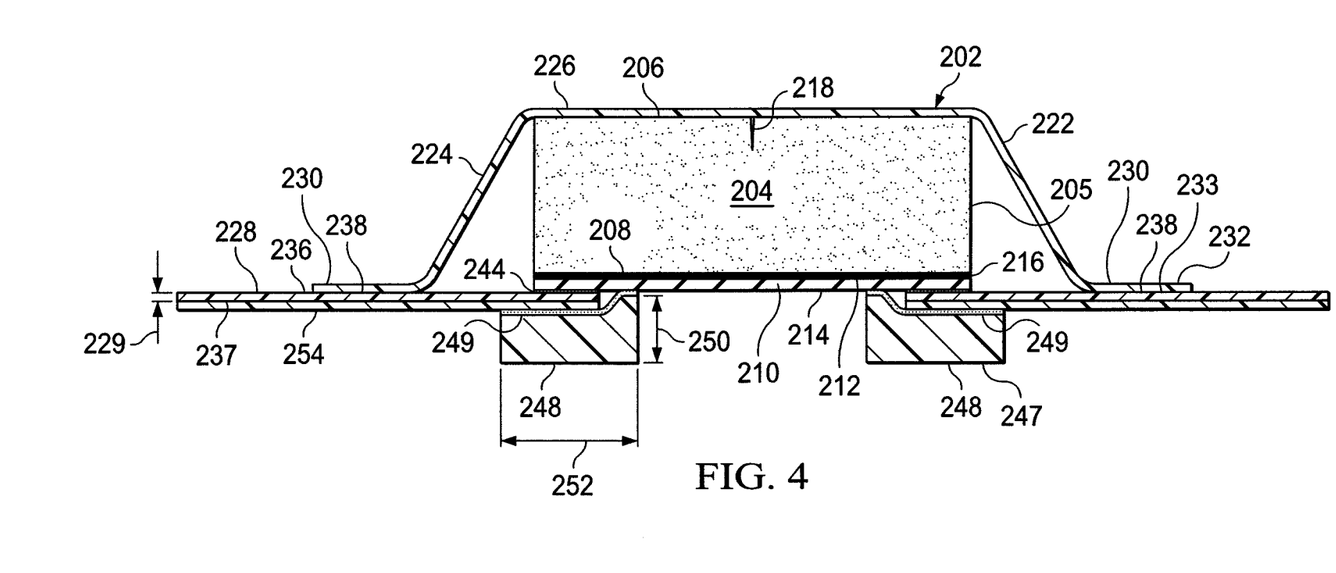
FIG. 4 is a schematic cross section of an illustrative embodiment of a dressing assembly.

Referring now primarily to FIGS. 3-4, a portion of a reduced-pressure treatment system 200 for treating a linear wound, area wound, other wound, or graft is presented. The portion of the reduced-pressure treatment system 200 is shown in FIG. 3 in a pre-deployment state.

The reduced-pressure treatment system 200 includes a dressing assembly 202, which includes a dressing bolster 204. The dressing bolster 204 has a first side 206 and a second, inward-facing side 208. The dressing bolster 204 may be formed from any medical bolster material, or manifold material, as previously referenced. A comfort layer 210, which has a first side 212 and a second, inward-facing side 214, may be coupled, e.g., by a heat bond 216 or any other technique, to the second, inward-facing side 208 of the dressing bolster 204.

The comfort layer 210 may be any material that helps prevent skin irritation and discomfort while allowing fluid transmission through the comfort layer 210. Suitable materials for the comfort layer 210 have been mentioned in connection with comfort layer 124 of FIGS. 1-2. The comfort layer 210 may include anti-microbial substances, such as silver. The comfort layer 210 may be made like a breathable, dry layer.

In one illustrative embodiment, the dressing bolster 204 may include a plurality of flexibility notches 218. The flexibility notches 218 may extend partially (e.g., ⅛, ¼, ½, ¾) through the dressing bolster 204 or completely through. The flexibility notches 218 may be lateral notches, or lateral cuts, in the dressing bolster 204 and, in addition or alternatively, may be one or more longitudinal notches, or longitudinal cuts, or other cuts. The cuts may be made using a saw (or notched blade), a hot knife, or other device. The flexibility notches 218 enhance flexibility of the dressing bolster 204. The enhanced flexibility may be particularly useful when the dressing assembly 202 is applied over a patient's joint or other area of movement. For example, if the dressing bolster 204 is used on a knee, the dressing bolster 204 may need to flex or extend as much as 100% or more. The flexibility notches 218 help provide flexibility. In addition, a plurality of folds 220 or bellows may be added to facilitate movement.

The dressing bolster 204 may have lateral edges 205 that are orthogonal with respect to the second, inward-facing side 208 of the dressing bolster 204. The lateral edges 205 may also be shaped, e.g., beveled or angled or rounded. The lateral edge 205, when angled, may be between 10 and 90 degrees with respect to the second, inward-facing side of the dressing bolster 204. The shaped lateral edges 205 may help reduced shear stress between the patient's epidermis and the dressing bolster 204. Other dimensions, steps, and processes may be used.

In one illustrative embodiment, the dressing bolster 204 is manufactured as follows. A foam block of Granufoam® material, e.g., 1.21 meter×1.8 meter×0.5 meter block, is cut to have a 19 mm height, and a saw is used to form lateral grooves, or lateral flexibility notches 218. Then, a dry layer, which may be the comfort layer 210, is laminated or attached onto the second, or bottom, surface. Then, the foam block is cut using a die cut to form the individual dressing bolsters 204.

A sealing subsystem 222 provides a fluid seal over the dressing assembly 202 and at least a portion of the patient's epidermis. The sealing subsystem 222 includes an sealing member 224, which may be formed with a first sealing member portion 226 (or upper drape portion for the orientation shown in FIG. 4) and a second sealing member portion 228 (or lower drape portion for the orientation shown in FIG. 4). The first sealing member portion 226 extends over the first side 206 of the dressing bolster 204 and extends further to form a drape flange, or drape extension 230, which has a first side 232 and a second, inward-facing side 233. An aperture 234 (FIG. 3) is formed on a portion of the first sealing member portion 226. The aperture 234 allows fluid communication with a reduced-pressure interface (analogous to reduced-pressure interface 138 in FIG. 1).

The second, inward-facing side 233 of the drape extension 230 is placed on a first side 236 of the second sealing member portion 228 and coupled by an attachment device 238, such as by an adhesive, bond, weld (e.g., ultrasonic or RF weld), cements stitching, staples, other coupling means. The first sealing member portion 226 may include the plurality of folds 220 or bellows. The folds 220 allow the first sealing member portion 226 to expand if needed. For example, if the dressing assembly 202 is used on a joint, when the joint is flexed, the first sealing member portion 226 is extended using the folds 220. Additional drape material may be released from the folds 220 to facilitate movement. The folds 220 may also be formed as ridges that in cross section would appear as accordion-like ridges that flatten out when stretched and thereby provide additional material.

The second, inward-facing side 237 of the second sealing member portion 228 may have an attachment apparatus or device on a portion. The second sealing member portion 228 has a treatment area aperture 240 (FIG. 5).

One or more release members 242 may be releasably coupled to the first side 236 of the second sealing member portion 228. Four release members 242 are shown in the illustrative embodiment of FIG. 3. The release members 242 provide stiffness or cover an attachment apparatus or the like to help during deployment of the dressing assembly 202. The release members 242 are typically either casting paper or a film held on the first side 236 of the second sealing member portion 228.

Figure 5:
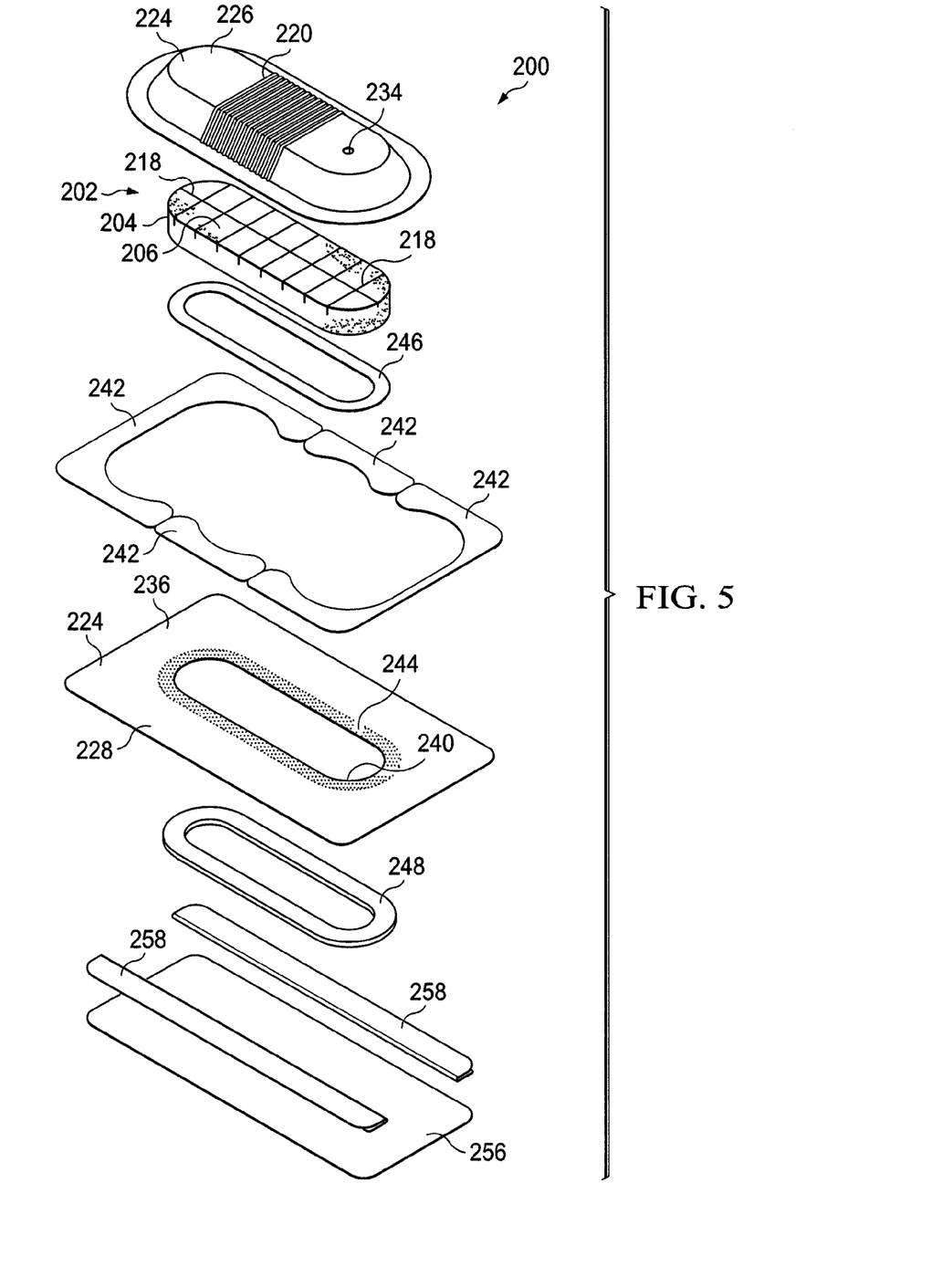
FIG. 5 is a schematic, exploded, perspective view of the illustrative embodiment of a dressing assembly of FIG. 4 in a pre-deployed state.

Referring now primarily to FIG. 5, an exploded perspective view of a portion of a reduced-pressure treatment system 200 for treating tissue, e.g., subcutaneous tissue, a linear wound, area wound, other wound, or graft is presented. The portion of the reduced-pressure treatment system 200 presented in FIG. 5 is shown in a pre-deployment state and in an exploded view. The portion of the reduced-pressure treatment system 200 includes the dressing assembly 202, which includes the dressing bolster 204. The dressing bolster 204 is the same as the dressing bolster 204 shown in FIGS. 3-4, but the flexibility notches 218 are both lateral and longitudinal.

The first side 206 of the dressing bolster 204 is covered by a portion of the sealing member 224, which includes a first sealing member portion 226. The sealing member 224 may also include a second sealing member portion 228. The first sealing member portion 226 may include folds 220 and an aperture 234. The second sealing member portion 228 is formed with a treatment area aperture 240 that provides an opening for at least a portion of the dressing bolster 204 (or a comfort layer) to be directly against a patient's epidermis or treatment site. The second sealing member portion 228 has first side 236 and may have an adhesive 244 applied on a portion of the first side 236. The adhesive 244 may be used primarily during manufacture to retain the dressing bolster 204 against the second sealing member portion 228 during assembly and also used to help retain the dressing bolster 204 during use. In assembly, prior to applying the dressing bolster 204 against the adhesive 244, the adhesive 244 is covered by a center release member 246. Outboard of the adhesive 244 on the first side 236 are release members 242 that provide stiffness to the sealing member 224 during deployment.

A portion of the second, inward-facing side 237 (FIG. 4) of the second sealing member portion 228 (or an adjacent layer) may be covered with the sealing ring 248. The sealing ring 248 may comprise a sealing material such as the sealing materials previously mentioned in connection with sealing ring 117 or other material that provides initial tack between the dressing assembly 202 and the patient's epidermis. The sealing material may have a softness (or hardness) in the range of 20-90 Shore OO, and more typically between 70 and 80 Shore OO. The sealing ring 248 helps seal any wrinkles or discontinuities in the epidermis or drape that might otherwise cause leaks. As shown best in FIG. 4, the sealing ring 248 may have a thickness 250 and a width of 252. The thickness 250 of the sealing ring 248 is typically in the range of 0.3-2.5 mm and more typically 0.7-1.25 mm. The width of the sealing ring 248 is typically in the range of about 10-30 mm, but other widths are possible. In one illustrative embodiment, the thickness 250 is about 0.7 mm and the width is about 20 mm. For contrast, the second sealing member portion 228 typically has a thickness 229 in the range of about 0.178 mm-0.254 mm (about 7-10 mils). The ratio of the sealing ring thickness 250 to the sealing member thickness 229 may be in the range of about 2.75 to about 7.03. The sealing ring 248 may be formed with fenestrations or apertures. In another embodiment, the sealing ring 248 may comprise a patterned sealing material on the second, inward-facing side 214 of the comfort layer 210 or the second, inward-facing side 208 of the dressing bolster 204. The pattern may be spaced islands or crossing lines of sealing material or any other pattern.

The sealing ring 248 may be coupled to the second sealing member portion 228, which may include sealing device 254, or coupled to the comfort layer 210 (see FIG. 8) or both as shown in FIG. 4. The sealing ring 248 may be coupled directly or may be coupled using an optional sealing-ring attachment device 249, such as an acrylic adhesive, cement, or other coupling device. The sealing ring 248 may function as a two-sided gasket that seals between the dressing bolster 204 (or comfort layer 210) and sealing ring 248 and between the sealing ring 248 and the patient's epidermis. The sealing ring 248 may also form a seal between the sealing ring 248 and second sealing member portion 228. The sealing ring 248 may absorb perspiration or other fluids from the patient.

The sealing ring 248 may help distribute shear forces created by the application of reduced pressure at the interface of the dressing bolster 204 and the patient' epidermis. The modulus of elasticity of sealing ring 248 may be between that of the second sealing member portion 228 and the patient's epidermis. The sealing ring 248 may be entirely and directly underneath (for the orientation shown in FIG. 4) the dressing bolster 204 as suggested in FIG. 8 or may straddle an extreme edge of the dressing bolster 204 as shown in FIG. 4 to further help distribute shear stress. While reference is made to a "ring," it should be understood that discrete members including linear members may make up the sealing ring 248.

As shown clearly in FIG. 4, a portion of the second, inward-facing side 237 of the second sealing member portion 228 may be covered with the sealing apparatus or device 254, such as an adhesive. With reference to FIGS. 4 and 5, when in the pre-deployment state, the sealing device 254 is covered by a bottom release member 256 and side release members 258.

Referring primarily to FIGS. 3-5, according to an illustrative embodiment, in use, the bottom release liner 256 is removed, and the exposed sealing device 254, e.g., adhesive, on the second, inward-facing side 237 of the second sealing member portion 228 and an exposed inward-facing surface 247 of the sealing ring 248 are placed against a portion of the patient's epidermis. The sealing device 254, e.g., adhesive, and sealing ring 248 are secured around a linear wound on the patient's epidermis. After smoothly applying the second sealing member portion 228, the side release members 258 are removed. The release members 242 on the first side 236 of the second sealing member portion 228 are removed. A reduced-pressure interface is coupled to the aperture 234 in the first sealing member portion 226. (The center release member 246 was previously removed during manufacture). Reduced pressure is then delivered.

With respect to manufacturing the systems and components described above, in applying and coupling a sealing member to the first surface of a dressing bolster, it may be desirable to utilize a press to remove any wrinkles that may otherwise result or remain. The medical bolster material of the shaped dressing assembly may be cut using a die cut or by hand with a router.

Figure 6A:
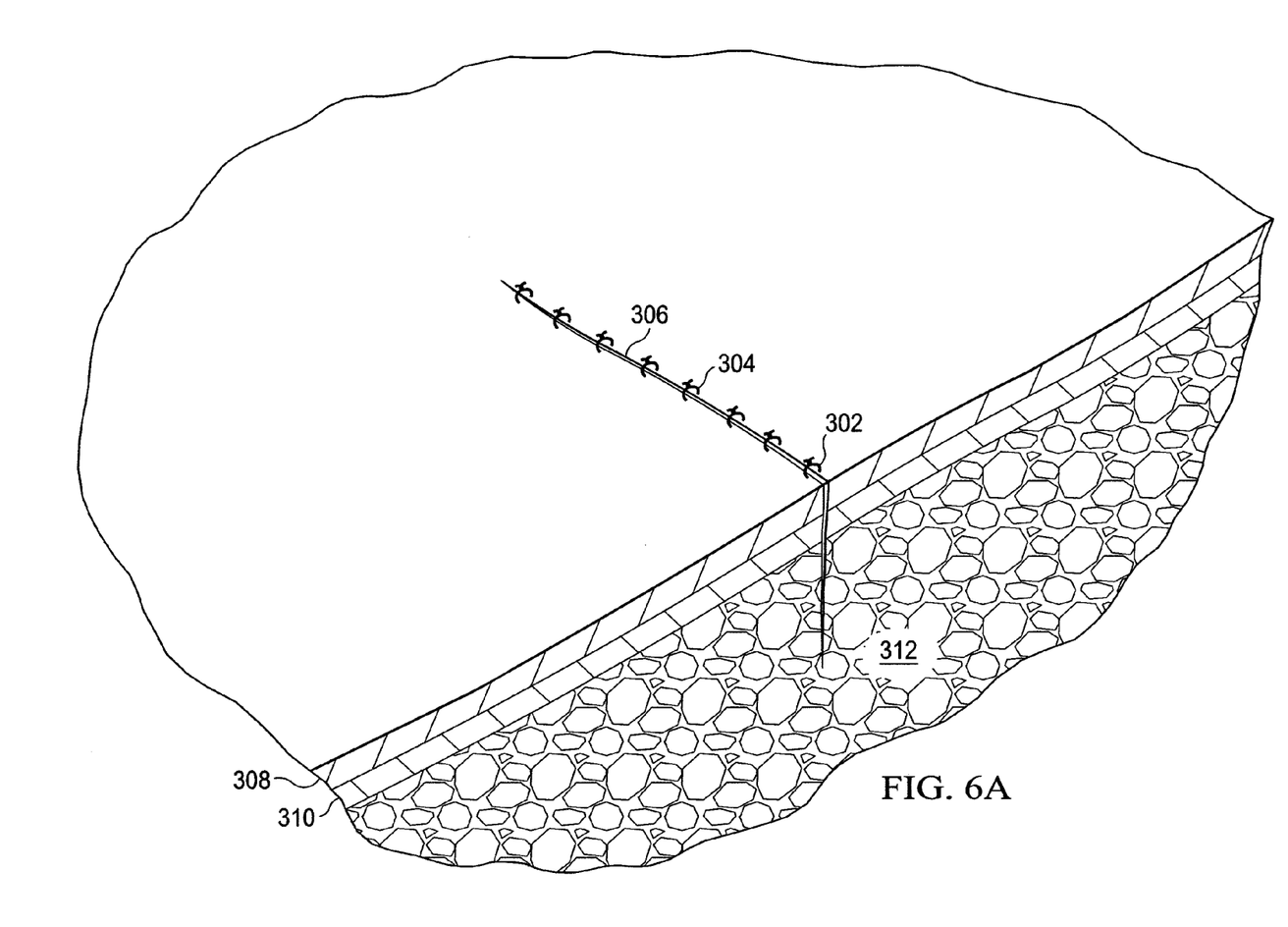
FIGS. 6A-C are perspective views (with a portion shown in cross section) of a portion of a reduced-pressure treatment system being deployed over a linear wound.
Figure 6B:
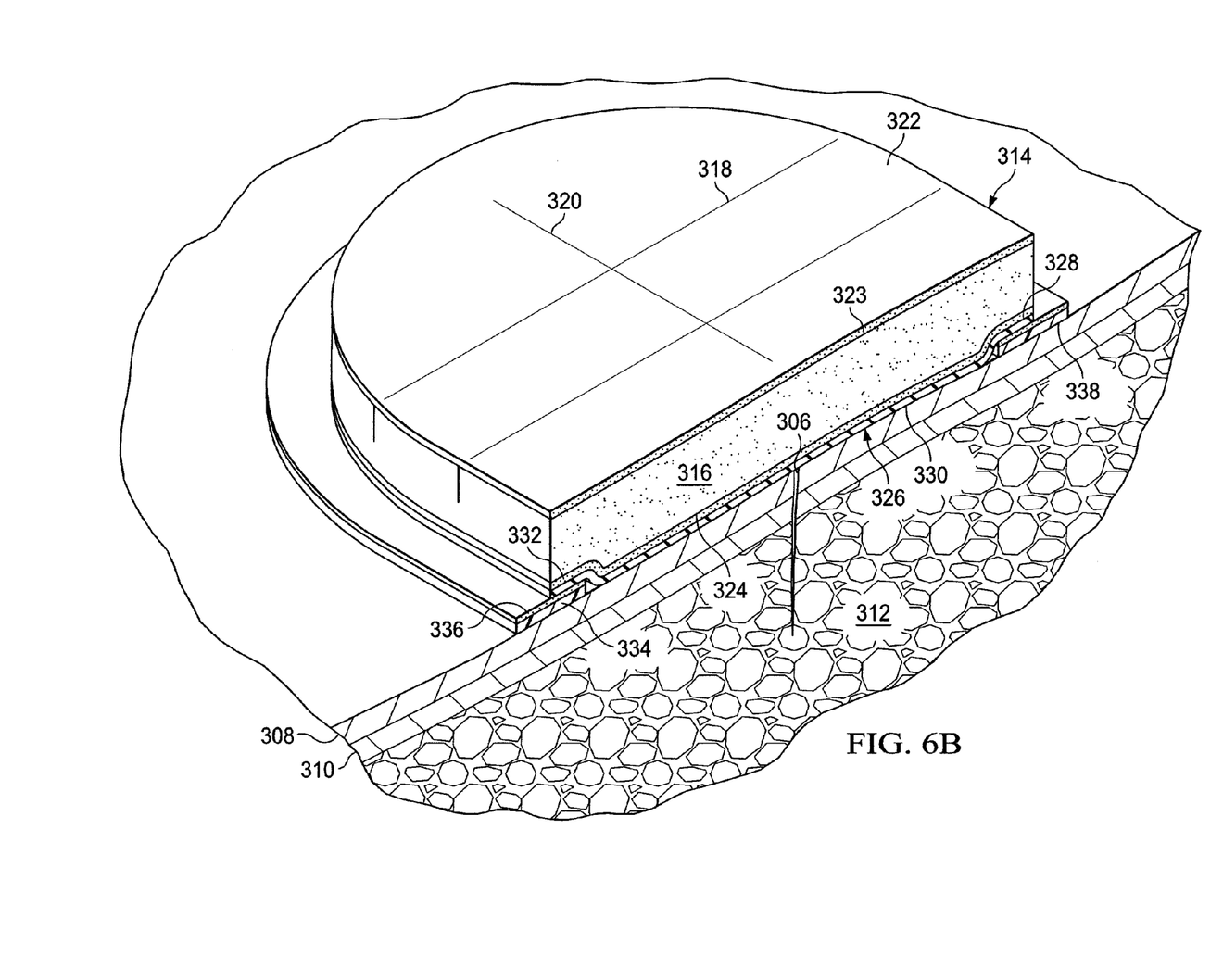
Figure 6C:
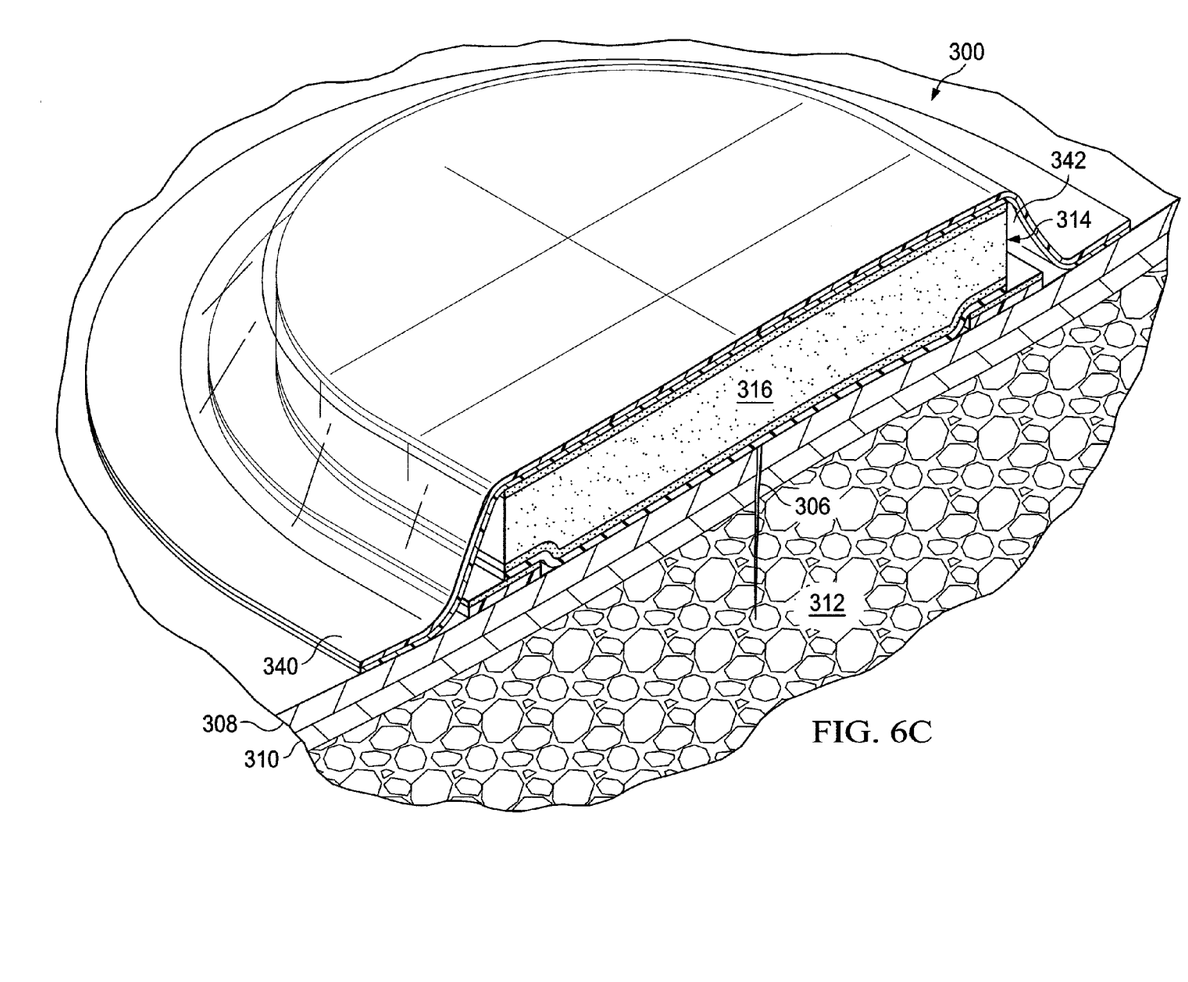

Referring now primarily to FIGS. 6A-6C, another illustrative embodiment of a portion of a reduced-pressure system 300 is presented. With the reduced-pressure system 300 of FIGS. 6A-6C, aspects of the reduced-pressure system 300 are assembled in stages at a linear wound 306. In FIG. 6A, a closure device 302, e.g., stitches 304, close the illustrative linear wound 306. Other closure devices 302 may be used such as epoxy or staples. The linear wound 306 may include a portion through a patient's epidermis 308, dermis 310, and subcutaneous tissue 312.

Referring now to FIG. 6B, after the linear wound 306 is prepared, a bolster assembly 314 is disposed proximate to the linear wound 306. The bolster assembly 314 may include a dressing bolster 316. The dressing bolster 316 may be formed from the bolster or manifold materials previously mentioned. The dressing bolster 316 may include a plurality of lateral notches 318 and one or more longitudinal notches 320. The dressing bolster 316 has a first side 322 and a second, inward-facing side 324. The first side 322 may include an adhesive layer 323. The adhesive layer 323 may help secure a sealing member 340 thereto.

The bolster assembly 314 may include a comfort layer 326. The second, inward-facing side 324 of the dressing bolster 316 may be covered with the comfort layer 326. The comfort layer 326 has first side 328 and a second, inward-facing side 330. The first side 328 of the comfort layer 326 may be coupled by an attachment device 332, e.g., heat bond, adhesive, weld, or other attachment technique, to the second, inward-facing side 324 of the dressing bolster 316.

The bolster assembly 314 includes a sealing ring 334 or a sealing ring 334 may be applied around the linear wound 306 before the dressing bolster 316 is applied. With the former, the sealing ring 334 may be coupled, at least in part, to the second, inward-facing side 330 of the comfort layer 326. The sealing ring 334 may be analogous to sealing ring 248 of FIGS. 3-5. The sealing ring 334 may adhere on its own to the comfort layer 326 or may be coupled with sealing-ring attachment device 336 to the comfort layer 326. The sealing-ring attachment device 336 may be, for example, acrylic adhesive, cement, or other attachment means. The sealing ring attachment device 336 may be co-extensive with the comfort layer 326 or may extend beyond a lateral edge of the dressing bolster 316. Prior to application, an inward-facing surface 338 of the sealing ring 334 may be covered by a release liner (not shown). The release liner is removed, and the sealing ring 334 is centered about the linear wound 306.

Referring now to FIG. 6C, a sealing member 340 is disposed over the bolster assembly 314 and a portion of the patient's epidermis 308 to form a sealed space 342. An aperture may then be formed or is preformed (analogous to aperture 234 in FIG. 3). A reduced-pressure interface (not shown but analogous to reduced-pressure interface 138) is coupled to the sealing member 340 to provide fluid communication with the sealed space 342 through the aperture. A reduced-pressure source (not shown but analogous to reduced-pressure source 144 in FIG. 1) is coupled by a reduced-pressure delivery conduit (not shown but analogous to reduced pressure delivery conduit 148 in FIG. 1) to the reduced-pressure interface to provide reduced pressure to the sealed space 342 to treat the linear wound 306.

Figure 7:
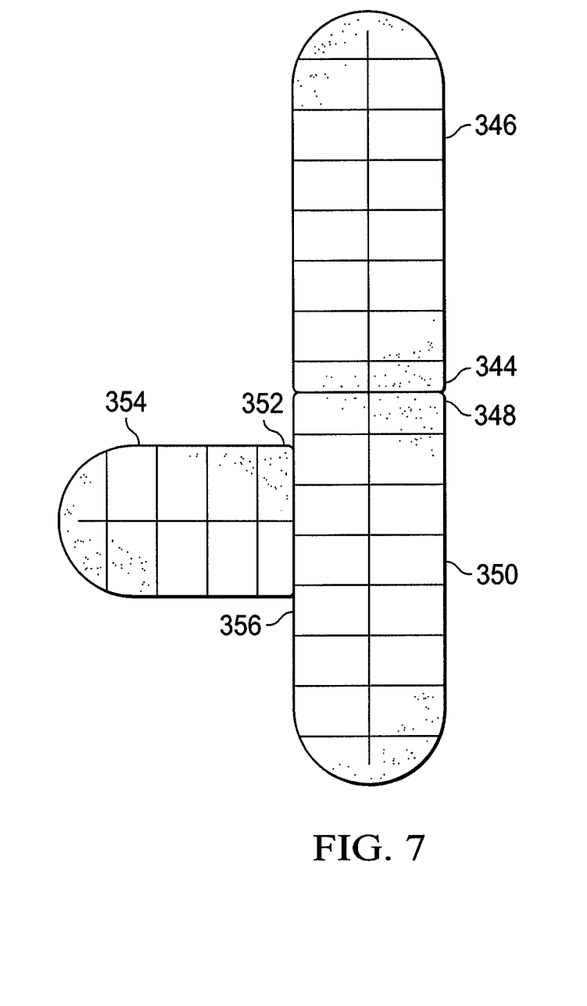
FIG. 7 is a schematic, top view of an illustrative embodiment of a portion of a system for treating a linear wound with reduced pressure.

The bolster assembly 314 may be cut to accommodate different sizes of linear wounds 306 prior to being disposed on the linear wound 306 and covered with a sealing member 340. As shown in FIG. 7, for lengthy linear wounds 306 or multiple linear wounds 306 in a vicinity, more than one bolster assembly 314 may be used. Continuing to refer to FIG. 7, a first longitudinal end 344 of a first bolster assembly 346 has been cut to have a flat surface. A first longitudinal end 348 of a second bolster assembly 350 has been cut or otherwise formed with a flat surface. The first longitudinal end 344 of the first bolster assembly 346 is placed proximate to and abutting the first longitudinal end 348 of the second bolster assembly 350. The sealing rings (not shown but analogous to sealing ring 334) below the first bolster assembly 346 and second bolster assembly 350 may, with time, coalesce or combine to form an integral ring.

A first longitudinal end 352 of a third bolster assembly 354 has been placed proximate to and abutting a lateral end or edge 356 of the second bolster assembly 350. Once the combination of bolster assemblies is arranged, the bolster assemblies 346, 350, 354 are covered with a sealing member (not shown but analogous to sealing member 340 in FIG. 6C) to form a sealed spaced. The sealed space contains the bolster assemblies 346, 350, 354. Reduced pressure may be then be applied to the sealed space to treat the linear wound or wounds.

Figure 8:
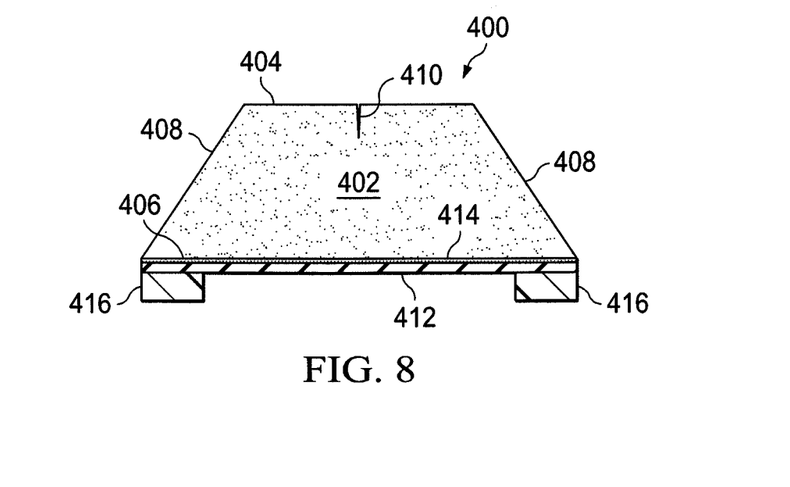
FIG. 8 is a schematic cross section of an illustrative embodiment of a dressing assembly.

Referring now primarily to FIG. 8, a cross section of an illustrative bolster assembly 400 is shown. The bolster assembly 400 may be used with reduced-pressure treatment systems, such as reduced-pressure treatment system 200. The bolster assembly 400 includes a dressing bolster 402. The dressing bolster 402 has a first side 404, a second side (inward-facing) 406, and lateral edges 408. As with the previously presented bolster assemblies, the lateral edges 408 may take any shape, but are shown formed with approximately a 45 degree angle with respect to the second, inward-facing side 406. In the cross-section, a longitudinal notch 410 is visible. In addition, lateral notches may be included on the first side 404 and notches may be added to the lateral edges 408. The longitudinal notch 410 and any other notches help provide flexibility to the bolster assembly 400.

A comfort layer 412 is coupled by an attachment device 414 to the second, inward-facing side 406 of the dressing bolster 402. A sealing ring 416 is shown coupled to the comfort layer 412. The sealing ring 416 may be formed from the sealing materials previously mentioned. The sealing ring 416 may adhere on its own to the comfort layer 412 or may be attached by an attachment device such as an acrylic adhesive (not shown).

As before, in use, the bolster assembly 400 may be placed over and about a linear wound and then covered with a sealing member to form a sealed space. Reduced pressure may then be delivered to the sealed space to treat the linear wound with reduced pressure.

Figure 9:
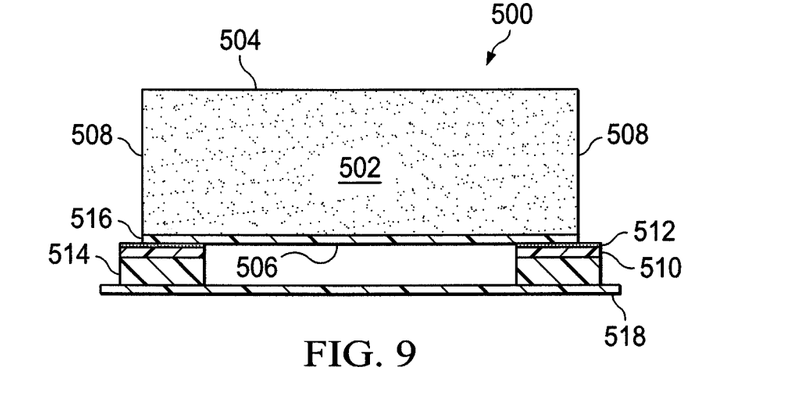
FIG. 9 is a schematic cross section of an illustrative embodiment of a dressing assembly.

Referring now primarily to FIG. 9, another bolster assembly 500 is shown in cross section. The bolster assembly 500 is analogous in most respect to the bolster assembly 400 of FIG. 8. The bolster assembly 500 includes a dressing bolster 502 having a first side 504 and a second, inward-facing side 506. The lateral edges 508 are substantially orthogonal to the second, inward-facing side 506, but like the dressing bolster 402 of FIG. 8, could take on any angle or shape. In this embodiment, a sealing ring 514 is laminated or coupled to a drape ring 510. The drape ring 510 assists with positioning and manipulating the sealing ring 514 during assembly. The drape ring 510 is coupled by an attachment device 512 to the second, inward-facing side 506 of the dressing bolster 502 or to an inward-facing side of a comfort layer 516. The sealing ring 514 may be covered by a release liner 518 prior to use.

In another embodiment (not explicitly shown), an attachment device, e.g., an adhesive, may be applied to the second, inward-facing side of a sealing ring to provide tackiness or enhanced tackiness between the sealing ring and the patient's epidermis. The attachment device may be particularly beneficial when the sealing ring comprises a harder hydrocolloid than those previously mentioned or when applied in cold conditions and the sealing material needs time to warm up to become adequately tacky.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in connection to any one embodiment may also be applicable to any other embodiment.

It will be understood that the benefits and advantages described above may relate to one embodiment or may relate to several embodiments. It will further be understood that reference to "an" item refers to one or more of those items.

The steps of the methods described herein may be carried out in any suitable order, or simultaneously where appropriate.

Where appropriate, aspects of any of the examples described above may be combined with aspects of any of the other examples described to form further examples having comparable or different properties and addressing the same or different problems.

It will be understood that the above description of preferred embodiments is given by way of example only and that various modifications may be made by those skilled in the art. The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of the claims.

We claim:

1. A system for treating a linear wound on a patient, the system comprising:
   a dressing assembly, the dressing assembly comprising:
      a dressing bolster having a first side and a second, inward-facing side,
      a comfort layer coupled to the second, inward-facing side of the dressing bolster,
      a first sealing member portion covering the dressing bolster,
      a second sealing member portion covering a portion of the second, inward-facing side of the dressing bolster and extending outward from the dressing bolster to form a drape extension, wherein a portion of the first sealing member is coupled to the second sealing member,
      a sealing ring disposed adjacent to the second, inward-facing side of the dressing bolster, and
      wherein the first sealing member portion, second sealing member portion, and sealing ring form a sealed space over the linear wound; and a reduced-pressure source for fluidly coupling to the sealed space.

2. The system of claim 1, wherein the sealing ring is formed from a sealing material having a hardness in the range of 70-80 Shore (type OO).

3. The system of claim 1, wherein the sealing ring has a thickness $T_{sr}$ that is in the range 0.7-1.25 mm.

4. The system of claim 1, wherein the sealing ring has a thickness $T_{sr}$, the second sealing member portion has a thickness $T_{sm}$, and the ratio of $T_{sr}/T_{sm}$ is in the range of about 2.7 to 7.0.

5. The system of claim 1, wherein the sealing ring comprises a sealing material laminated onto a drape ring and further comprising an adhesive coupling the drape ring to the comfort layer or to the dressing bolster.

6. The system of claim 1, wherein the dressing bolster comprises at least two discrete members placed with abutting edges and wherein the sealing ring comprises at least two discrete members that have coalesced to form an integral member.

7. The system of claim 1, wherein the sealing ring comprises a sealing material, and wherein the sealing material comprises at least one of the following: hydrocolloids, hydrogels, silicone polymers, and natural gums (xanthan, guar, cellulose).

8. The system of claim 1, wherein the dressing bolster has lateral edges formed at an angle other than 90 degrees with respect to the second, inward-facing side of the dressing bolster.

9. The system of claim 1, wherein the dressing bolster has lateral edges formed at an angle between 20 to 50 degrees with respect to the second, inward-facing side of the dressing bolster.

10. The system of claim 1, wherein the sealing ring is coupled to at least a portion of the second, inward-facing side of the comfort layer.

11. The system of claim 1, wherein the sealing ring is coupled to at least a portion of the second sealing member portion.

12. The system of claim 1, wherein the sealing ring extends beyond a lateral edge of the dressing bolster.

13. A method for treating a linear wound on a patient with reduced pressure, the method comprising:
    extruding a sealing material around the linear wound to form a sealing ring;
    disposing a dressing bolster proximate to the linear wound and coupled to at least a portion of the sealing material;
    covering the dressing bolster and a portion of the patient's epidermis with a sealing member to create a sealed space; and
    delivering reduced pressure to the sealed space.

14. The method of claim 13, wherein the sealing material has a hardness in the range of 70-80 Shore (type OO).

15. The method of claim 13, wherein the sealing ring has a thickness $T_{sr}$ that is in the range 0.7-1.25 mm.

16. The method of claim 13, wherein the sealing ring has a thickness $T_{sr}$, the sealing member has a thickness $T_{sm}$, and the ratio of $T_{sr}/T_{sm}$ is in the range of about 2.7 to 7.0.

17. The method of claim 13, wherein the sealing material comprises at least one of the following: hydrocolloids, hydrogels, silicone polymers, and natural gums (xanthan, guar, cellulose).

18. A method for treating a linear wound of a patient with reduced pressure, the method comprising:
    disposing a bolster assembly proximate to the linear wound, wherein the bolster assembly comprises:
        a dressing bolster having a first side and a second, inward-facing side,
        a comfort layer coupled to the second, inward-facing side of the dressing bolster, and
        a sealing ring coupled to the second, inward-facing side of the comfort layer;
    covering the bolster assembly with a sealing member to form a sealed space containing the dressing assembly; and
    introducing reduced pressure into the sealed space.

19. The method of claim 18, wherein the sealing ring extends beyond a lateral edge of the dressing bolster.

20. The method of claim 18, wherein the sealing material has a hardness in the range of 70-80 Shore (type OO).

21. The method of claim 18, wherein the sealing ring has a thickness $T_{sr}$ that is in the range 0.7-1.25 mm.

22. The method of claim 18, wherein the sealing ring has a thickness $T_{sr}$, the sealing member has a thickness $T_{sm}$, and the ratio of $T_{sr}/T_{sm}$ is in the range of about 2.7 to 7.0.

23. The method of claim 18, wherein the sealing material comprises at least one of the following: hydrocolloids, hydrogels, silicone polymers, and natural gums (xanthan, guar, cellulose).

24. The method of claim 18,
    wherein the dressing bolster comprises a first dressing bolster having a first end and a second dressing bolster having a first end; and
    wherein the step of disposing the bolster assembly comprises disposing the first dressing bolster over at least a portion of the linear wound and disposing the second dressing bolster over at least a portion of the linear wound, wherein the first end of the first dressing bolster abuts the first end of the second dressing bolster.

25. The method of claim 18,
    wherein the dressing bolster comprises a first dressing bolster having a first end and a second dressing bolster having a first end;
    wherein the step of disposing the bolster assembly comprises disposing the first dressing bolster over at least a portion of the linear wound and disposing the second dressing bolster over at least a portion of the linear wound, wherein the first end of the first dressing bolster abuts the first end of the second dressing bolster;
    wherein the sealing ring comprises a first sealing ring and a second sealing ring;
    wherein the first sealing ring is coupled to the first dressing bolster and the second sealing ring is coupled to the second dressing bolster; and
    wherein the first sealing ring and second sealing ring touch and become an integral sealing ring.

26. A system for treating a linear wound on a patient comprises:
    a dressing bolster assembly comprising:
        a dressing bolster having a first side and a second, inward-facing side,
        a comfort layer coupled to the second, inward-facing side of the dressing bolster, wherein the comfort layer has a first side and a second, inward-facing side, and
        a sealing ring coupled to the second, inward-facing side of the comfort layer;
    a sealing member disposed over the dressing bolster for creating a sealed space; and
    a reduced-pressure source fluidly coupled to the sealed space.

* * * * *